(12) United States Patent
Diamond

(10) Patent No.: US 9,869,630 B2
(45) Date of Patent: Jan. 16, 2018

(54) METHODS AND SYSTEMS FOR MONITORING ROADWAY PARAMETERS

(71) Applicant: Maxim Sokol Diamond, Croton on Hudson, NY (US)

(72) Inventor: Maxim Sokol Diamond, Croton on Hudson, NY (US)

(*) Notice: Subject to any disclaimer, the term of this patent is extended or adjusted under 35 U.S.C. 154(b) by 0 days.

(21) Appl. No.: 14/888,052

(22) PCT Filed: Apr. 30, 2014

(86) PCT No.: PCT/US2014/036203
§ 371 (c)(1),
(2) Date: Oct. 29, 2015

(87) PCT Pub. No.: WO2014/179481
PCT Pub. Date: Nov. 6, 2014

(65) Prior Publication Data
US 2016/0076991 A1    Mar. 17, 2016

Related U.S. Application Data

(60) Provisional application No. 61/817,357, filed on Apr. 30, 2013.

(51) Int. Cl.
*G01M 17/02* (2006.01)
*G01N 19/08* (2006.01)
(Continued)

(52) U.S. Cl.
CPC .............. *G01N 19/08* (2013.01); *G01P 15/00* (2013.01); *G01S 19/13* (2013.01); *G06Q 10/20* (2013.01); *G06Q 50/30* (2013.01)

(58) Field of Classification Search
None
See application file for complete search history.

(56) References Cited

U.S. PATENT DOCUMENTS

| | | | |
|---|---|---|---|
| 5,880,362 A * | 3/1999 | Tang | G01M 17/007 188/DIG. 1 |
| 9,108,640 B2 | 8/2015 | Jackson | |

(Continued)

FOREIGN PATENT DOCUMENTS

| EP | 1566665 A1 | 8/2005 |
|---|---|---|

OTHER PUBLICATIONS

Media Centre for Jaguar Land Rover (Jun. 10, 2015) Jaguar Land Rover Announces Technology Research Project to Detect, Predict and Share Data on Potholes, 2 pages. http://newsroom.jaguarlandrover.com/en-in/jlr-corp/news/2015/06/jlr_pothole_alert_research_100615/.

(Continued)

*Primary Examiner* — Andre Allen
(74) *Attorney, Agent, or Firm* — Tarter Krinsky & Drogin LLP

(57) ABSTRACT

A method and system receives, at a computing device, a plurality of data points from one or more data collection units. Each data point of the plurality of data points can include data related to road conditions for a specific section of road and each data point can be paired with GPS coordinates. The plurality of data points can be analyzed and a road condition score for each data point can be determined. The road condition score for each data point is applied to a mapping module using the GPS coordinates.

20 Claims, 6 Drawing Sheets

(51) Int. Cl.
*G06Q 10/00* (2012.01)
*G06Q 50/30* (2012.01)
*G01P 15/00* (2006.01)
*G01S 19/13* (2010.01)

(56) References Cited

U.S. PATENT DOCUMENTS

| | | | |
|---|---|---|---|
| 9,165,093 B2* | 10/2015 | Imamura | B60C 99/006 |
| 2003/0033071 A1 | 2/2003 | Kawasaki | |
| 2005/0141294 A1 | 11/2005 | Cerwin | |
| 2007/0008090 A1 | 1/2007 | Gertsch et al. | |
| 2008/0024323 A1 | 1/2008 | Kadaba | |
| 2010/0271191 A1* | 10/2010 | de Graff | B60C 23/0408 340/447 |
| 2011/0052042 A1 | 3/2011 | Ben Tzvi | |
| 2011/0026439 A1 | 10/2011 | An | |
| 2013/0016106 A1 | 1/2013 | Yip et al. | |
| 2015/0184348 A1 | 7/2015 | Stracke, Jr. | |
| 2015/0210286 A1* | 7/2015 | Hanatsuka | B60C 99/00 701/34.4 |
| 2015/0260614 A1* | 9/2015 | Forslof | G08G 1/0112 702/182 |
| 2015/0284006 A1* | 10/2015 | Singh | B60C 23/02 702/41 |

OTHER PUBLICATIONS

European Office Action dated Jun. 20, 2017.

\* cited by examiner

METHODS AND SYSTEMS FOR MONITORING ROADWAY PARAMETERS

FIELD OF THE DISCLOSURE

The disclosed technology relates to methods and systems for monitoring road parameters, and more particularly, to methods and systems for monitoring pavement and environmental conditions surrounding vehicles.

BACKGROUND INFORMATION

Civil infrastructure, construction and maintenance represent a large societal investment. Construction and road maintenance often occurs after damage to the roads and pavement, which can be due to, e.g., traffic and weather. Roadway work zones used for assessment and repair are a major source of traffic congestion, which results in lost productivity and waste. For example, lanes are often closed on highways and bridges for construction or repair, which can lead to major traffic congestion.

Current methods of road quality monitoring are reactive. Potholes and other road quality issues are usually fixed after they are spotted. Road quality issues are usually found as discoveries by road maintenance crews or through voluntary reports by drivers. Specialized vehicles are also sometimes used, but often these are slow, can cause traffic congestion, and do not provide for a measure of modularity that allows for monitoring of other road parameters besides road quality.

Thus, there is a need for methods and systems to monitor road and pavement conditions at an early stage so that repair can be provided before major potholes or other damage is caused. Further, there is a need for detecting parameters other than road and/or pavement quality.

SUMMARY

The present disclosure describes methods and systems that can provide for continuous monitoring of road parameters, e.g. the methods and systems can allow for the detection of road quality patterns that indicate future roadway disruptions or allow road maintenance crews to be proactive rather than reactive.

In one implementation, a computer-implemented method comprises the steps of: receiving, at a computing device, a plurality of data points from at least one data collection unit, each data point including data related to road conditions for a specific section of road, and each data point being paired with GPS coordinates; analyzing the plurality of data points; determining a road condition score for each data point; and applying the road condition score for each data point to a mapping module using the GPS coordinates. In some implementations, each data point can be recorded at a regularly-spaced sampling period, e.g., a defined time or a defined distance.

In other implementations, the road condition score can be a standard deviation value calculated for each data point of the plurality of data points. The standard deviation value can be matched to the GPS coordinates to evaluate and model road roughness for a specific section of road. The standard deviation value for each data point can be visualized using a GIS system. That is, the standard deviation value can be color-coded for a specific section of road on a road condition map. The road condition map can be provided to a client device, e.g., a smartphone, computer display or some other visual display, for personal usage or used by municipalities for road monitoring services.

In some implementations, the computing device can be integrated with a vehicle computer system or the computing device can be remote from the data collection unit and the computing device receives the plurality of data points over a wireless communication system.

In some implementations, the data collection unit can be a smartphone or an accelerometer. In some implementations, the data collection unit can include a storage module for storing the plurality of data points and the GPS coordinates. In some implementations, the data collection unit can be mounted to a vehicle.

In another implementation, a system comprising: one or more processors; one or more computer-readable storage mediums containing instructions configured to cause the one or more processors to perform operations including: receiving, at a computing device, a plurality of data points from at least one data collection unit, each data point including data related to road conditions for a specific section of road, and each data point being paired with GPS coordinates; analyzing the plurality of data points; determining a road condition score for each data point; and applying the road condition score for each data point to a mapping module using the GPS coordinates.

In some implementations, the road condition score can be a standard deviation value calculated for each data point of the plurality of data points. The standard deviation value can also be matched to the GPS coordinates to evaluate and model road roughness for the specific section of road specific.

In another implementation, a computer-program product, the product tangibly embodied in a machine-readable storage medium, including instructions configured to cause a data processing apparatus to: receive, at a computing device, a plurality of data points from at least one data collection unit, each data point including data related to road conditions for a specific section of road, and each data point being paired with GPS coordinates; analyze the plurality of data points; determine a road condition score for each data point; and apply the road condition score for each data point to a mapping module using the GPS coordinates. In some implementations, the road condition score can be a standard deviation value calculated for each data point of the plurality of data points and the standard deviation value is matched to the GPS coordinates to evaluate and model road roughness for the specific section of road specific.

The methods and systems according to the present disclosure can allow for real-time assessments of road quality and conditions, air quality, nearby traffic conditions, weather conditions, radiation, noise, vehicle speed/trajectory and/or insolation.

Figure 1:
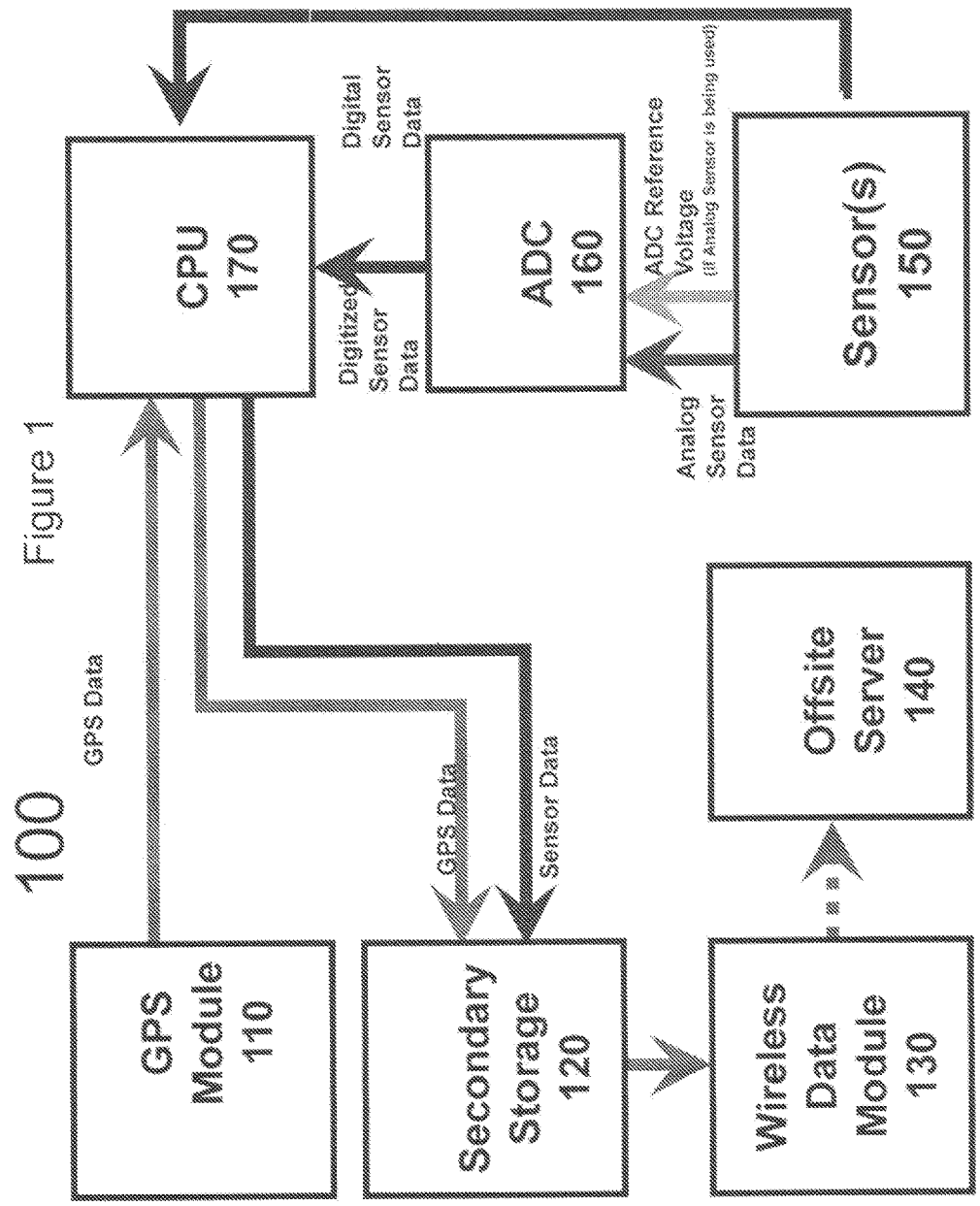
FIG. 1 is a block/flow diagram of a system for monitoring road parameters as disclosed in the specification.

Throughout the figures, the same reference numerals and characters, unless otherwise stated, are used to denote like features, elements, components or portions of the illustrated implementations. Moreover, while the subject disclosure will now be described in detail with reference to the figures, it is done so in connection with the illustrative implementations. It is intended that changes and modifications can be made to the described implementations without departing from the true scope and spirit of the subject disclosure.

DETAILED DESCRIPTION

FIG. 1 illustrates a block diagram of a system 100 for monitoring road parameters according to the present disclosure. One or more data collection units, e.g., sensors, 150 can be mounted on a vehicle, e.g., cars, trucks, motorcycles, bicycles, or any other mode of transportation used on roads. For example, the sensors 150 can be placed on or installed within the vehicle, e.g., pre-installed by factory during manufacture, or installed by the consumer sometime thereafter.

If the sensor 150 is an accelerometer, the accelerometer can be located on or nearby a hard mounting point thereby reducing unwanted vibrations. Multiple mounting points, close to the sensor, and/or a thicker PCB also help to reduce the effect of system resonance on the performance of the sensor.

In one implementation, the sensor can placed on the dashboard of a car with Velcro or the sensor could also be placed on the undercarriage of the car in close proximity to a wheel rim and held in place using a weather-resistant epoxy. In some implementations, a multiplicity of sensors may be used. The sensors 150 can be placed at different locations and mounted using a variety of mounting methods depending on the intended application.

The various sensors can be used to log road quality parameters, such as but not limited to accelerometers to measure road quality, carbon dioxide sensors to measure air quality, and any other sensor for detection of the road/pavement or the air or traffic surrounding the vehicle.

In one implementation, if an accelerometer is used, the accelerometer can have a complete 3-axis acceleration measurement system with selectable measurement ranges, e.g., ±2 g, ±4 g, ±8 g, or ±16 g. The accelerometer can measure both dynamic acceleration resulting from motion or shock and static acceleration that allows the device to be used as a tilt sensor. The sensor, for example, can be a polysilicon surface-micromachined structure built on top of a silicon wafer. Polysilicon springs can suspend the structure over the surface of the wafer and provide a resistance against forces due to applied acceleration. Deflection of the structure is measured using differential capacitors that consist of independent fixed plates and plates attached to the moving mass. Acceleration deflects the proof mass and unbalances the differential capacitor, resulting in a sensor output whose amplitude is proportional to acceleration. Phase-sensitive demodulation is used to determine the magnitude and polarity of the acceleration. The accelerometer can also have several special sensing functions, e.g., to sense activity and inactivity, to detect the presence or lack of motion by comparing the acceleration on any axis with pre-defined thresholds, to detect tap sensing and be used to detect single and double taps in any direction, to measure static acceleration of gravity in tilt-sensing applications and dynamic acceleration resulting from motion or shock. The accelerometer can also have a high resolution (3.9 mg/LSB) that enables measurement of inclination changes less than 1.0°.

In other implementations, other parameters can be measured using different data collection units, such as road quality/conditions, air quality, nearby traffic conditions, weather conditions, radiation, noise, vehicle speed/trajectory and/or insolation, and the present disclosure is not limited to any particular data collection unit.

In one implementation, as a vehicle is traveling, the sensor(s) 150 can be used to obtain road pavement parameter data at a pre-determined sampling rate. The sampling rate can be measured in time or distance. For example, the sampling rate can take measurements every 0.2 seconds or every 50 feet, it is understood that other sampling rates are contemplated. The sampling rate can be dependent on, e.g., the rate of speed the car is traveling and the dynamics of the road, e.g., curves, straight, etc.

The data obtained by sensors 150 can be paired with a GPS Module 110 in a CPU 170 and the combination can be stored in a secondary storage module 120, such as but not limited to a vehicle computer, an SD card, or other type of memory. The secondary storage 120 can be separate from the computer processing unit ("CPU") 170. For example, a MicroSD card can be connected to the CPU 170 using an SPI interface. However, secondary storage 120 can be integrated with the CPU 170 if non-volatile memory present on-board the CPU 170 is large and fast enough.

A wireless data module 130, such as but not limited to a cellular, WiFi, or other wireless data communication protocol, can be provided where recorded data from the sensors 150 and/or secondary storage 120 can be uploaded to a central server 140 for analysis. This can be done when the vehicle is parked and no data is being logged (e.g., to conserve processing resources). This can also be done in real time, at a time preset by the user or manually by the user.

Figure 2:
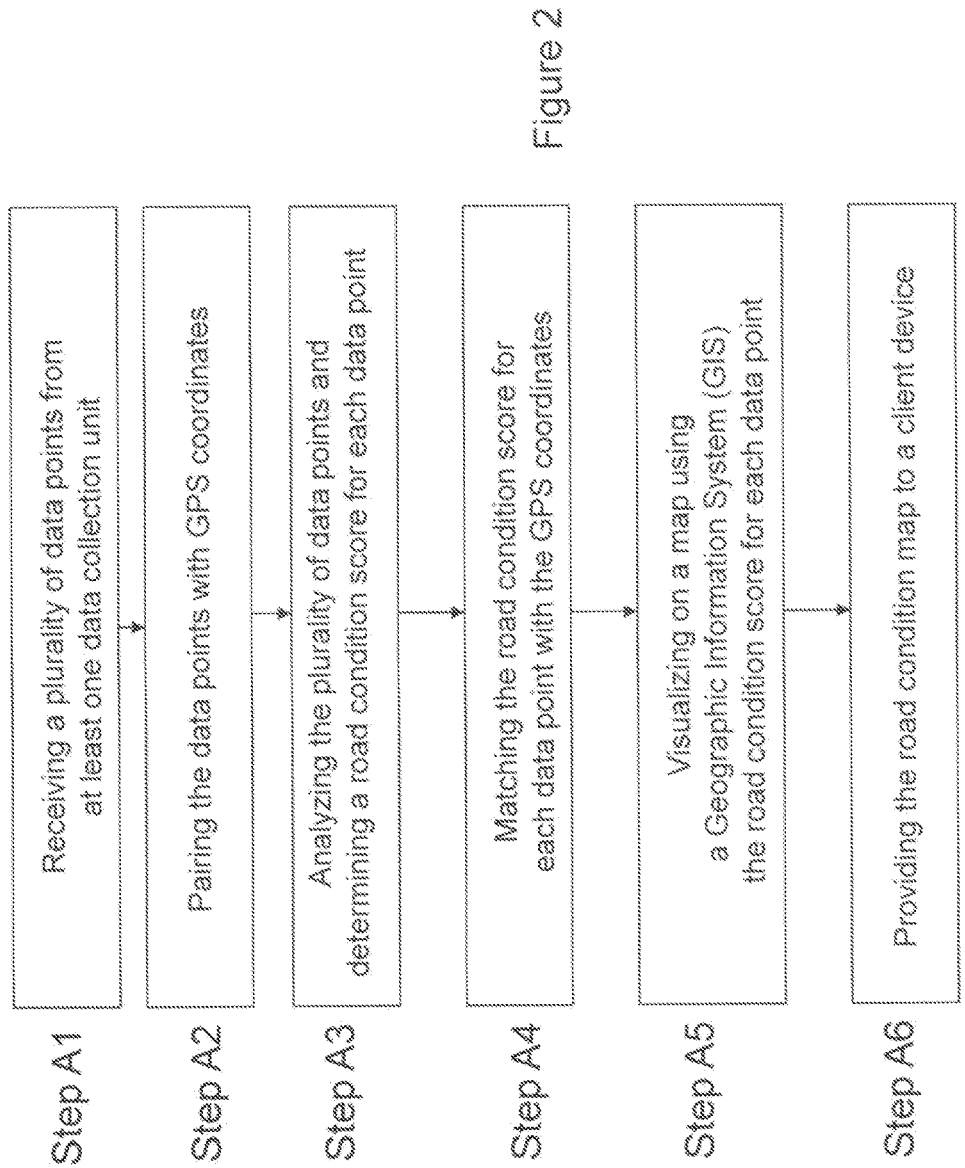
FIG. 2 is a flow chart showing a method for monitoring road parameters as disclosed in the specification.

As shown in FIG. 2, the central server 140 can receive a plurality of data points from at least one data collection unit 150. (Step A1). The central server 140 can be partially integrated with a vehicle computer system or the central server 140 can be independent and remote from the data collection unit 150 and receive the plurality of data points over a wireless communication system 130. Each data point of the plurality of data points can include data related to road conditions for a specific section of road. These data points can be paired with GPS coordinates. (Step A2). The central server 140 analyzes the plurality of data points and determines a road condition score for each data point. (Step A3). The road condition score can be, e.g., a standard deviation value calculated for each data point of the plurality of data points. In some implementations, road condition scores from multiple vehicles can be averaged to gain more accurate road condition scores. The road condition scores are matched to the GPS coordinates (Step A4) and can be used to evaluate road roughness for specific sections of roads, (e.g., a number of samples (e.g., 320 samples equating to approximately 1 mile of road) can be collected for a particular section of road; these samples are analyzed as a group and standard deviation values are tabulated for each sample within the group). The road condition score for each data point can be visualized on a map using a Geographic Information System (GIS) associated with the central server 140. (Step A5).

Figure 3:
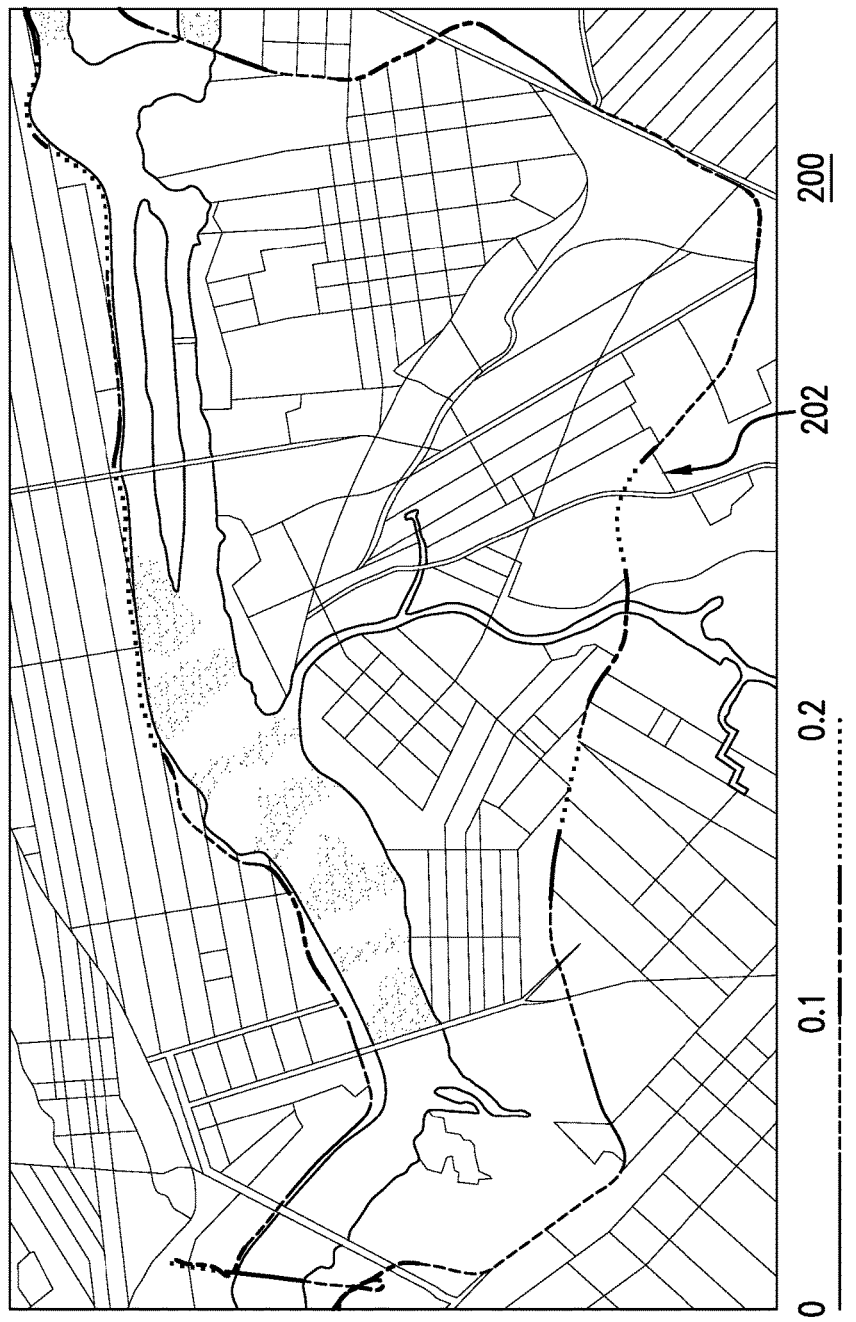
FIG. 3 is an illustration of a road condition map as disclosed in the specification.

As shown in FIG. 3, a standard deviation value can be color-coded based on magnitude and visualized on a specific section of road 202 on a road condition map 200. The road condition map 200 can be provided to a client device (Step A6), e.g. a smartphone, a computer monitor or some other visualization device.

Figure 4:
FIG. 4 is illustrations of road condition monitoring maps as disclosed in the specification.

The road condition map 200 can be used (1) to monitor road erosion of a roadway over time (e.g., see FIG. 4, Maps 300, 310, 320), (2) inform municipalities when a road has reached a certain level of road roughness and needs repair, (3) inform municipalities that potholes of a certain size have develop in the roadway and need immediate attention, and (4) predict the development of potholes, sinkholes or breaks in expansion joints. The road condition map can also be used by motorcycle and bicycle enthusiasts so that smooth roads can be mapped for excursions. The road condition map can also be used by insurance companies to evaluate a customer's profile and the road conditions in which the customer typically drives. The central server 140 or the CPU 170 can also be customized to issue a variety of reports, real time alerts regarding a driver's current navigation and routes, e.g., routes that avoid road hazards.

In some implementations, the CPU 170 can be located on the vehicle, and can read and record data stream(s) coming from the sensor(s) 150 and the GPS module 110, and can write data to the secondary storage 120. The CPU 170 can also be used to facilitate wireless data upload procedures through an interface with the wireless data module 130.

If the sensors 150 contain an analog sensor, an analog-to-digital converter ("ADC") 160 can be used to convert the analog data to digital data. Different analog sensors can operate at a variety of voltages, so that a reference voltage can be given to the ADC 160 so it can map data properly according to the operating voltage of the sensor. The ADC 160 can also be integrated with the CPU 170. If analog sensors are not being used, the ADC may not be used and can be left out of the systems for the present disclosure.

Figure 5:
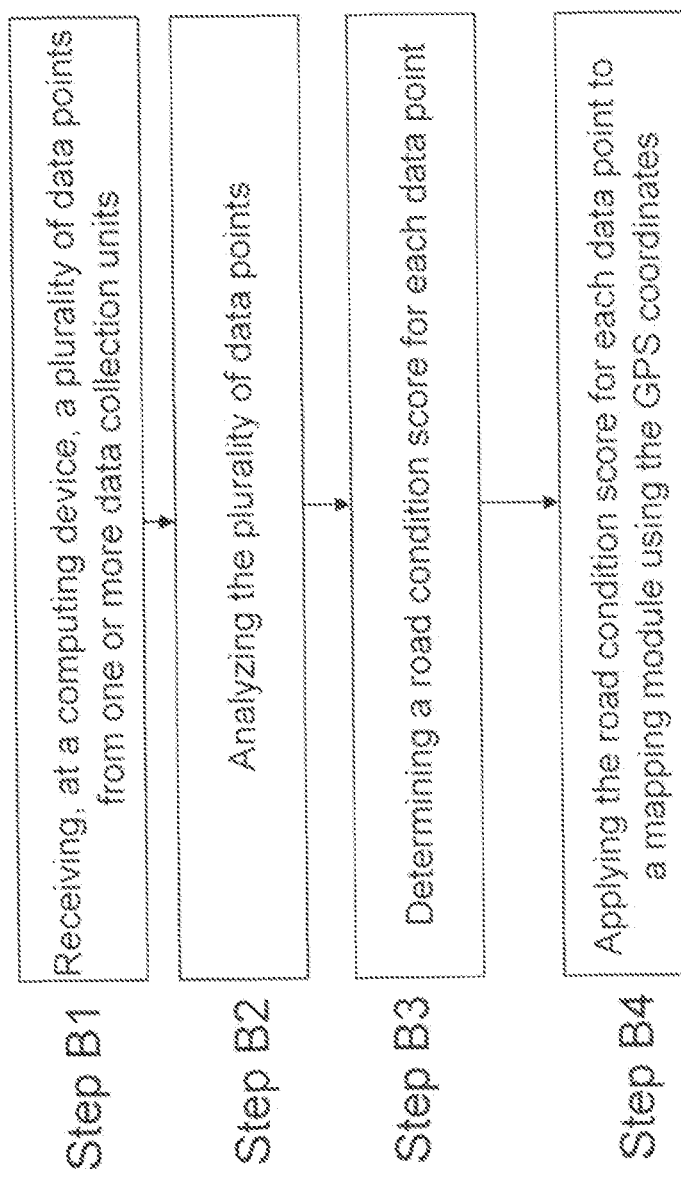
FIG. 5 is a flow chart showing a method for monitoring road parameters as disclosed in the specification.

FIG. 5 shows a flow chart for a method that receives, at a computing device, a plurality of data points from one or more data collection unit. (Step B1). Each data point of the plurality of data points can include data related to road conditions for a specific section of road and each data point can be paired with GPS coordinates. The plurality of data points can be analyzed (Step B2) and a road condition score for each data point can be determined. (Step B3). The road condition score for each data point is applied to a mapping module using the GPS coordinates. (Step B4).

Figure 6:
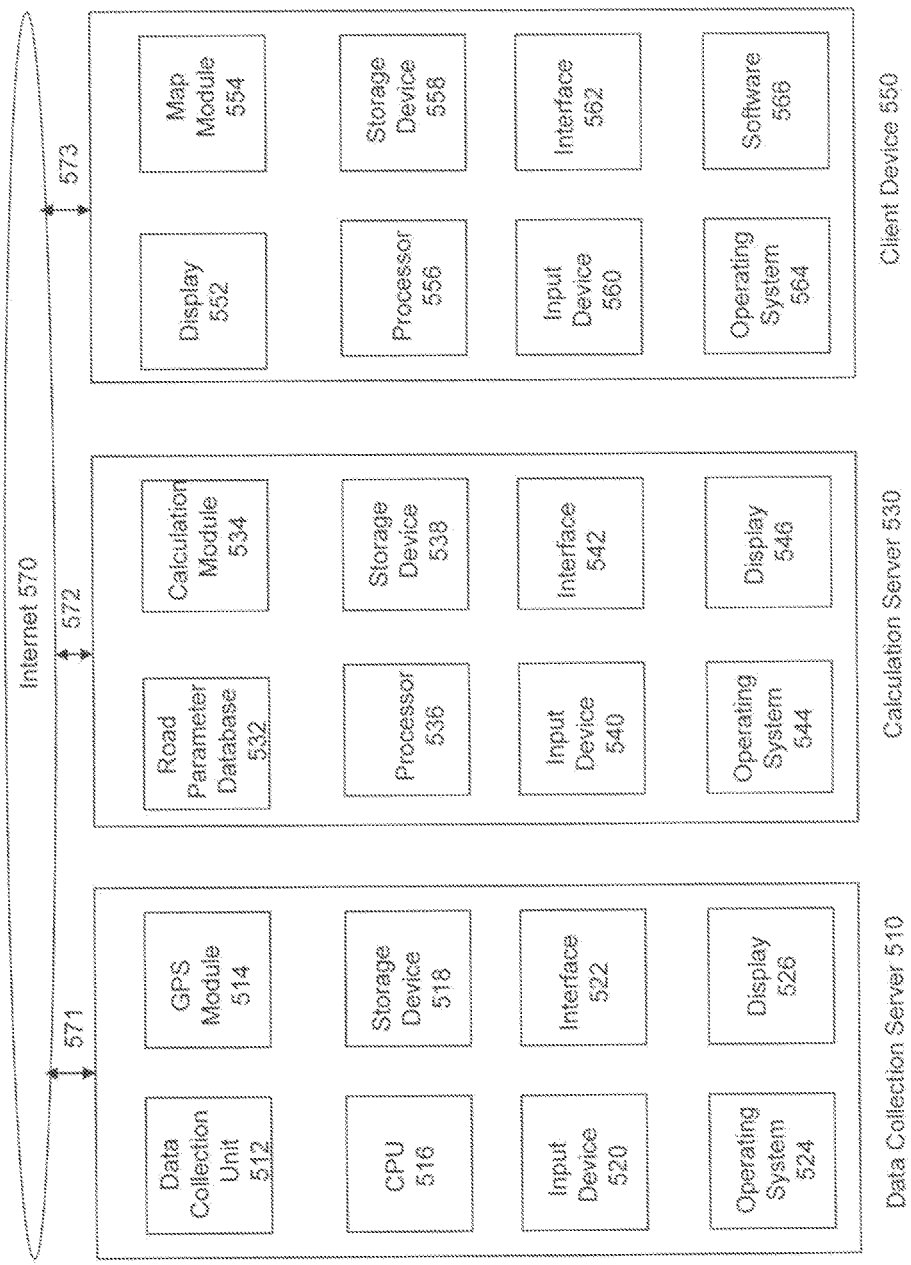
FIG. 6 shows a schematic diagram of an example of the disclosed technology.

FIG. 6 is a schematic diagram of an example of a monitoring roadway parameters system 500. The roadway monitoring system 500 includes a data collection server 510, a calculation server 530 and a client device 550. For ease of explanation only one of each device is shown but more than one of each is contemplated and combinations devices are also contemplated, e.g., the data collection server can be integrated with a client device.

The data collection server 510 can include a data collection unit 512, a GPS module 514, a CPU 516, a storage device 518, an input device 520, an interface 522, an operating system 524 and a display 526.

The calculation server 530 includes a road parameter database 532, calculation module 534, a processor 536, a storage device 538, an input device 540, an interface 542, an operating system 544 and a display 546.

The client device 550 includes a display 552, a map module 554, a processor 556, a storage device 558, an input device 560, an interface 562, an operating system 564 and software 566.

The data collection server 510, the calculation server 530 and the device 550 can be connected to one another over an internet connection 570 but more secure connections are contemplated.

In some implementations, the system of FIG. 5 can be is split into an environment communicatively connected over the internet 570 with connectors 571, 572, 573 where the one or more servers 510, 530 and devices 550 include hardware as shown in FIG. 5 and also code for providing algorithms used to calculate road roughness data, code for providing mapping functions, code for processing GPS coordinates, and code for interpreting data from the data collection unit.

The operating systems 524, 544, 564 can be multi-user, multiprocessing, multitasking, multithreading, real-time and the like. The operating systems 524, 544, 564 may perform basic tasks, including but not limited to: recognizing input from input devices 520, 540, 560; sending output to display devices 526, 546, 552; keeping track of files and directories on computer-readable mediums 518, 538, 558, 532 (e.g., memory or a storage device); controlling peripheral devices (e.g., disk drives, printers, etc.); and managing traffic on the one or more buses 571, 572, 573.

Various other considerations and modifications can be provided. For example, various microcontrollers, GPS units, storage devices, wireless communication modules, and user interface (UI) controls can be used, all of which can be enabled through software modification. The sensors and other components of the system according to the present disclosure can be integrated with the vehicle computer system to gain access to vehicle diagnostics and control functions. Various types of sensors can be used for any type of mobile sensing system that utilizes the inherent mobility of a vehicle. The system of the present disclosure can be used by various agencies, such as but not limited to municipalities, public transport systems, taxi cabs, mail/delivery services, insurance companies and/or public or private citizens.

Further, a smartphone can be used in lieu of the CPU 170, wireless data module 130, and/or secondary storage 120 if sensor orientation is not an issue for a specific implementation of the present disclosure. Sensors 150 on-board the smartphone can be used or peripheral devices can be used in conjunction with the smartphone.

The present disclosure can provide for a lower cost, a higher sampling rate, modularity, simplicity and/or higher accuracy when compared with monitoring systems of the prior art. Rather than relying on an event-based method of road quality monitoring, the present disclosure can upload all data to a central server in unmodified form. Data processing can be performed on the central server, which can free up processing power needs on the vehicle, allowing for the use of lower cost components and higher sensor sampling rates. Because of the modular nature of the design, different types of sensors can be used with the hardware of the present disclosure to monitor various parameters, including road quality.

Various other considerations can also be addressed in the exemplary applications described. For example, various computing arrangements can be provided, having a processor(s) configured or programmed to perform the steps and/or procedures of the present disclosure described above. Various data described above can be stored in various storage arrangements (e.g., hard drive, memory device, such as RAM, ROM, memory stick, floppy drive, other tangible computer-accessible medium, etc.). The processor(s) can access the storage arrangement(s) to execute a computer program or a set of instructions (stored on or in the storage arrangement) which can perform the procedures according to the methods and systems of the present disclosure.

It is noted that the systems and methods disclosed herein may be implemented on various types of computer architectures, such as for example on a single general purpose computer or workstation, or on a network (e.g., local area network, wide area network, or internet), or in a client-server configuration, or in an application service provider configuration. Also, the system's and method's data can be stored as one or more data structures in computer memory and/or storage depending upon the application at hand. The systems and methods may be provided on many different types of computer readable media including instructions being executable by a computer to perform the system and method operations described herein. The systems and methods may also have their information transmitted via data signals embodied on carrier signals (e.g., radio frequency carrier signals) or other communication pathways (e.g., fiber optics, infrared, etc.).

The computer components, software modules, functions and data structures described herein may be connected directly or indirectly to each other in order to allow the flow of data needed for their operations. It is also noted that a module includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The computer components may be located on a single computer or distributed across multiple computers depending upon the situation at hand.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the implementations shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising the steps of:
   receiving a plurality of data points from at least one accelerometer, each data point being paired with GPS coordinates, the at least one accelerometer including a three-axis acceleration measurement system that measures dynamic acceleration and static acceleration at a pre-determined sampling rate;
   storing the plurality of data points in a road parameter database;
   transforming the plurality of data points and GPS coordinates into road pavement parameter data using a calculation module, the road pavement parameter data including a road condition score related to road conditions for a specific section of road; and
   applying the road pavement parameter data to a mapping module.

2. The computer-implemented method of claim 1 wherein the pre-determined sampling rate is a defined time.

3. The computer-implemented method of claim 1 wherein the pre-determined sampling rate is a defined distance.

4. The computer-implemented method of claim 1 wherein the road condition score is a standard deviation value calculated for each data point.

5. The computer-implemented method of claim 4 wherein the standard deviation value is matched to the GPS coordinates to evaluate and model road roughness for the specific section of road.

6. The computer-implemented method of claim 5 wherein the standard deviation value for each data point is visualized in a GIS system.

7. The computer-implemented method of claim 6 wherein the standard deviation value is color-coded for the specific section of road on a road condition map.

8. The computer-implemented method of claim 7 further comprising the step of providing a road condition map to a client device.

9. The computer-implemented method of claim 1 wherein the at least one accelerometer is partially integrated with a vehicle computer system.

10. The computer-implemented method of claim 1 wherein the calculation module is remote from the at least one accelerometer and the calculation module receives the plurality of data points over a wireless communication system.

11. A system comprising:
    one or more processors;
    one or more computer-readable storage mediums containing instructions configured to cause the one or more processors to perform operations including:
    receive a plurality of data points from at least one accelerometer, each data point being paired with GPS coordinates, the at least one accelerometer including a three-axis acceleration measurement system that measures dynamic acceleration and static acceleration at a pre-determined sampling rate;
    store the plurality of data points in a road parameter database;
    transform the plurality of data points and GPS coordinates into road pavement parameter data using a calculation module, the road pavement parameter data including a road condition score related to road conditions for a specific section of road; and
    apply the road pavement parameter data to a mapping module.

12. The system of claim 11 wherein the pre-determined sampling rate is a defined time.

13. The system of claim 11 wherein the pre-determined sampling rate is a defined distance.

14. The system of claim 11 wherein the road condition score is a standard deviation value calculated for each data point.

15. The system of claim 14 wherein the standard deviation value is matched to the GPS coordinates to evaluate and model road roughness for the specific section of road.

16. The system of claim 15 wherein the standard deviation value for each data point is visualized in a GIS system.

17. The system of claim 16 wherein the standard deviation value is color-coded for the specific section of road on a road condition map.

18. The system of claim 17 further containing instructions configured to cause the one or more processors to perform operations including:
    provide a road condition map to a client device.

19. The system of claim 11 wherein the at least one accelerometer is partially integrated with a vehicle computer system.

20. The system of claim 11 wherein the calculation module is remote from the at least one accelerometer and the calculation module receives the plurality of data points over a wireless communication system.

* * * * *